(12) United States Patent
Verkaik

(10) Patent No.: US 11,529,100 B2
(45) Date of Patent: Dec. 20, 2022

(54) PRESSURE SENSITIVE DEVICE

(71) Applicant: RTM Vital Signs LLC, Fort Washington, PA (US)

(72) Inventor: Josiah Verkaik, Boise, ID (US)

(73) Assignee: RTM Vital Signs LLC, Philadelphia, PA (US)

( * ) Notice: Subject to any disclaimer, the term of this patent is extended or adjusted under 35 U.S.C. 154(b) by 818 days.

(21) Appl. No.: 16/423,608

(22) Filed: May 28, 2019

(65) Prior Publication Data

US 2019/0365327 A1 Dec. 5, 2019

Related U.S. Application Data

(60) Provisional application No. 62/679,117, filed on Jun. 1, 2018.

(51) Int. Cl.
| | | |
|---|---|---|
| *A61B 5/0215* | (2006.01) | |
| *A61B 5/00* | (2006.01) | |
| *A61B 5/0235* | (2006.01) | |
| *A61B 5/022* | (2006.01) | |

(52) U.S. Cl.
CPC .......... *A61B 5/6876* (2013.01); *A61B 5/0215* (2013.01); *A61B 5/0235* (2013.01); *A61B 5/02241* (2013.01); *A61B 5/6884* (2013.01); *A61B 2562/028* (2013.01)

(58) Field of Classification Search
None
See application file for complete search history.

(56) References Cited

U.S. PATENT DOCUMENTS

| | | | |
|---|---|---|---|
| 4,398,542 A | | 8/1983 | Cunningham et al. |
| 4,592,747 A | | 6/1986 | Pool |
| 4,825,876 A | | 5/1989 | Beard |
| 4,881,939 A | | 11/1989 | Newman |
| 4,920,972 A | | 5/1990 | Frank et al. |
| 5,044,203 A | | 9/1991 | Wiest et al. |
| 5,722,414 A | | 3/1998 | Archibald et al. |
| 7,340,288 B1 | * | 3/2008 | Karicherla ........... A61N 1/3627 600/374 |
| 8,360,984 B2 | | 1/2013 | Yadav et al. |
| 8,491,518 B2 | | 7/2013 | Schnell et al. |
| 2003/0097073 A1 | | 5/2003 | Bullister et al. |
| 2014/0213916 A1 | * | 7/2014 | Doan ................... A61B 5/0215 600/488 |
| 2015/0133796 A1 | | 5/2015 | Yadav |
| 2015/0289772 A1 | | 10/2015 | Huang et al. |

FOREIGN PATENT DOCUMENTS

JP    H03112534 A    5/1991

* cited by examiner

*Primary Examiner* — Meredith Weare
(74) *Attorney, Agent, or Firm* — Christopher & Weisberg, P.A.

(57) ABSTRACT

A pressure sensitive device including a body having a proximal portion and a distal portion opposite the proximal portion, the distal portion being made of a shape memory alloy, a flexible diaphragm at least partially surrounding the body and defining a fluid chamber between the flexible diaphragm and the distal portion of the body, and a non-compressible fluid disposed within the flexible diaphragm and exhibiting a hydraulic pressure in communication with the flexible diaphragm.

18 Claims, 8 Drawing Sheets

PRESSURE SENSITIVE DEVICE

CROSS-REFERENCE TO RELATED APPLICATION

This application is related to and claims priority to U.S. Provisional Patent Application Ser. No. 62/679,117, filed Jun. 1, 2018, entitled PRESSURE SENSITIVE DEVICE, the entirety of which is incorporated herein by reference.

FIELD

The present disclosure relates generally to pressure sensitive devices, and, more particularly, to a pressure sensitive device for communicating a hydraulic pressure within a blood vessel to a pressure measuring system outside of the blood vessel.

BACKGROUND

A patient's vital signs provide information useful for detecting and/or monitoring medical conditions. Known devices for measuring vital signs include, for example, blood pressure cuffs which attach to a patient's upper arm, pulse oximeters designed to be placed around the patient's fingertip, thermometers for measuring body temperature, stethoscopes for observing biological sounds, tonometers, and pressure transducers including those in the form of intravascular or transvascular devices having metal diaphragms.

Known pressure transducers typically include a housing containing a pressure measuring system, a diaphragm, and a substance, such as oil, for transferring a pressure exerted on the diaphragm to the pressure measuring system. The manufacturing of such pressure transducers may be difficult as a deflection of the diaphragm at the diaphragm's center should be no greater than a thickness of the diaphragm for accuracy. When a diaphragm is not the proper thickness, this may result inaccurate and incomplete readings of blood pressure which can significantly impact a patient's care and treatment.

Further, metal diaphragms are known to present problems, such as lack of sensitivity, in addition to various manufacturing limitations. For example, metal diaphragms having a diameter of approximately 1.0 millimeter are too small to compensate for relatively small variations in deflection leading to non-compliance. This can result in inaccurate and incomplete readings of a patient's blood pressure which may ultimately affect how a patient is cared for. Moreover, known transvascular devices typically necessitate the presence of significant hardware inside the blood vessel that may be hazardous for the patient including blood flow obstructions and the potential for thrombus formation. This can be extraordinarily dangerous for a patient and create risks and complications that may be avoidable.

SUMMARY

The present application provides for a pressure sensitive device including a body having a proximal portion and a distal portion opposite the proximal portion, the distal portion being made of a shape memory alloy, a flexible diaphragm at least partially surrounding the body and defining a fluid chamber between the flexible diaphragm and the distal portion of the body, and a non-compressible fluid disposed within the flexible diaphragm and exhibiting a hydraulic pressure in communication with the flexible diaphragm.

In another aspect of the invention, the non-compressible fluid is fluidly coupled to a pressure measuring system remote from the body, the pressure measuring system being configured to measure the hydraulic pressure exerted by a force on the flexible diaphragm.

In another aspect of the invention, the proximal portion and the distal portion of the body define an axis extending therethrough, and the distal portion of the body includes a plurality of arms extending therefrom.

In another aspect of the invention, the body includes a constrained configuration and an expanded configuration, the constrained configuration including the plurality of arms being parallel to the axis and the expanded configuration including the plurality of arms being disposed transverse with respect to the axis.

In another aspect of the invention, the body includes a transition region having the plurality of arms extending therefrom.

In another aspect of the invention, the transition region and the plurality of arms define a first curved region therebetween, and the plurality of arms define a second curved region opposite the first curved region.

In another aspect of the invention, the plurality of arms each define a length and an aperture extending along the length.

In another aspect of the invention, the flexible diaphragm is an elastomeric balloon and the non-compressible fluid is a silicone.

In another configuration, the present application provides a pressure sensing system having a pressure sensitive device including a tubular body having a transition region including a plurality of expandable arms extending therefrom, the plurality of expandable arms including a length and defining a planar region extending at least partially along the length, a diaphragm surrounding the plurality of expandable arms, the diaphragm defining a fluid chamber between the diaphragm and the tubular body, and a non-compressible fluid disposed within the fluid chamber and configured to exhibit a hydraulic pressure on the diaphragm. The pressure sensing system may also include a housing remote from and in communication with the pressure sensitive device, the housing including a pressure measuring system disposed therein, and the pressure measuring system including a MEMS device configured to be in communication with the hydraulic pressure exhibited by the non-compressible fluid.

In another aspect of the invention, the tubular body of the pressure sensitive device includes a proximal portion, a distal portion including the plurality of expandable arms opposite the proximal portion, and an axis extending therethrough.

In another aspect of the invention, the plurality of expandable arms of the pressure sensitive device are made of a shape memory alloy and include an expanded configuration when disposed within a blood vessel, the expanded configuration including the plurality of expandable arms being disposed transverse with respect to the axis.

In another aspect of the invention, the tubular body of the pressure sensitive device defines a fluid channel extending from the proximal portion to the distal portion.

In another aspect of the invention, the transition region of the tubular body of the pressure sensitive device defines a first curved region and the plurality of expandable arms define a second curved region opposite the first curved region.

In another aspect of the invention, the planar region of the plurality of expandable arms of the pressure sensitive device is between the first curved region and the second curved region, and the first curved region partially define an aperture extending along the planar region.

In another aspect of the invention, the tubular body of the pressure sensitive device defines an outer diameter between 0.8 millimeters to 1.1 millimeters.

In another aspect of the invention, the diaphragm of the pressure sensitive device is an elastomeric balloon and the non-compressible fluid is a silicone fluid.

In another aspect of the invention, the pressure measuring system includes a MEMS device.

In another aspect of the invention, the plurality of expandable arms of the pressure sensitive device include a pair of arms extending away from each other.

In another embodiment, the present invention provides a pressure sensitive device for communicating a hydraulic pressure within a blood vessel to an outside of the blood vessel, the pressure sensitive device having a body including a proximal portion and a distal portion opposite the proximal portion, the proximal portion and the distal portion defining a major axis extending therethrough, a plurality of arms extending from the distal portion of the body, a constrained configuration including the plurality of arms being parallel to the major axis, and an expanded configuration including the plurality of arms being perpendicular with respect to the major axis.

In another aspect of the invention, the body is configured to be at least partially inserted within a blood vessel wall and includes a transduction balloon surrounding at least a portion of the body, the transduction balloon defining a fluid chamber between the body and the transduction balloon and a fluid enclosed within the fluid chamber for exerting the hydraulic pressure on the transduction balloon.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
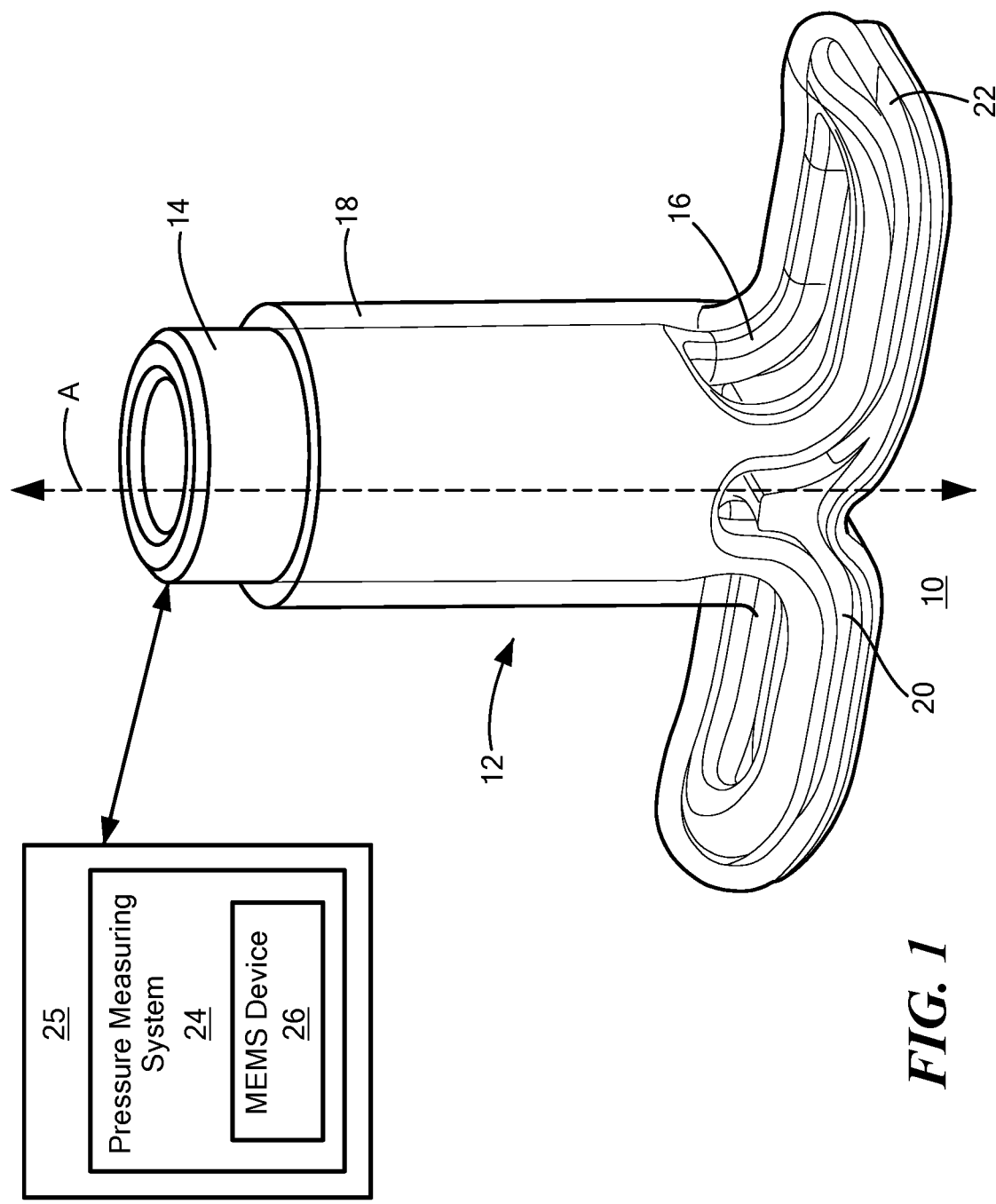
FIG. 1 is a perspective view of a pressure sensitive device including a body and a diaphragm at least partially surrounding the body in accordance with the present disclosure.

Before describing in detail exemplary embodiments, it is noted that the claims reside primarily in combinations of device and system components related to a pressure sensitive device for communicating a hydraulic pressure within a blood vessel to a pressure measuring system outside of the blood vessel. Accordingly, the device and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawings in which like reference designators refer to like elements there is shown in FIG. 1 an exemplary pressure sensitive device generally designated as "10." The pressure sensitive device 10 may be referred to herein as "the device 10" and is configured to be at least partially implanted in a blood vessel of a patient, such as a human or animal patient, for communicating a hydraulic pressure within the blood vessel to a pressure measuring system outside of the blood vessel.

In one configuration, the device 10 includes a body 12 having a proximal portion 14 and a distal portion 16 opposite the proximal portion 14, the proximal portion 14 and the distal portion 16 defining a major axis or axis "A" extending therethrough. The distal portion 16 is configured to extend through a wall of a blood vessel or blood vessel wall, i.e., the distal portion is transvascular. When extending through the wall, the distal portion 16 is configured to be oriented parallel to the axis A and, once inside the blood vessel, a portion of the distal portion 16 is configured to expand to an orientation perpendicular to the axis A. For example, during implantation into the blood vessel, the device 10 may be disposed within a delivery lumen (not shown) in a constrained configuration including the proximal and distal portions 14 and 16 being disposed along the axis A such that the proximal portion 14 and the distal portion 16 are oriented parallel to the axis A. The removal of the lumen transitions the device 10 from the constrained configuration to, as shown in FIG. 1, an expanded configuration including at least a portion of the distal portion 16 of the body 12 being transverse or perpendicular with respect to the axis A. As such, the distal portion 16 of the body 12 exhibits a larger profile in the expanded configuration than when in the constrained configuration. In an alternative embodiment, the distal portion 16 of the body 12 may be movable into a variety of different positions such that it be moved into different positions such that it may accommodate a particular patient's vascular structure. For example, the distal portion 16 of the body 12 may be moveable between the expanded configuration and the constrained configuration and may be secured using a securing device into a variety of different positions.

Referring still to FIG. 1, a flexible diaphragm 18 at least partially surrounds the body 12. The entirety of the distal portion 16 and at least a portion of the proximal portion 14 may be configured to extend outside of the blood vessel. The diaphragm 18 defines a fluid chamber 20 between the diaphragm 18 and the body 12. The diaphragm 18 may be a compliant balloon and a non-compressible fluid 22 or transduction fluid, such as a silicone fluid, may be disposed within the fluid chamber 20. The fluid chamber 20 may be a variety of different sizes and shapes depending upon the orientation of the vasculature that the device 10 is being used within.

When the device 10 is implanted within the blood vessel, the fluid 22 is configured to exhibit a hydraulic pressure in communication with the diaphragm 18 to facilitate the transfer of a pressure or force exerted on the diaphragm 18 from the blood vessel to a pressure measuring system 24 located on an outside of the blood vessel. The term "hydraulic pressure" generally refers to fluid in a confined space, i.e., a closed system, wherein the fluid is in a medium that can transmit force. This is in accordance with the discovery of French scientist-philosopher Blaise Pascal that a pressure applied to any part of a confined fluid transmits to every other part with no loss. The pressure acts with equal force on all equal areas of the confining walls in a direction perpendicular to the wall surfaces. In other words, the hydraulic pressure within the blood vessel is communicated to the pressure measuring system 24 located external to the blood vessel. In one configuration, the pressure measuring system 24 is disposed within a housing 25 and includes a Micro-Electro-Mechanic Systems ("MEMS") device 26, however, other types of pressure measurement devices configured to measure hydraulic pressure are within the scope of the present disclosure. The pressure measuring system 24 may be wired or wirelessly in electronic communication with a controller, a processor, a power source, and other electronic circuitry (not shown) configured to operate the pressure measuring system 24. In one configuration, the pressure measuring system 24 may be fluidly coupled with the fluid 22 and disposed remotely from the patient's body. The pressure measuring system 24 may be configured to measure the hydraulic pressure exerted by a force on the diaphragm 18.

Figure 2:
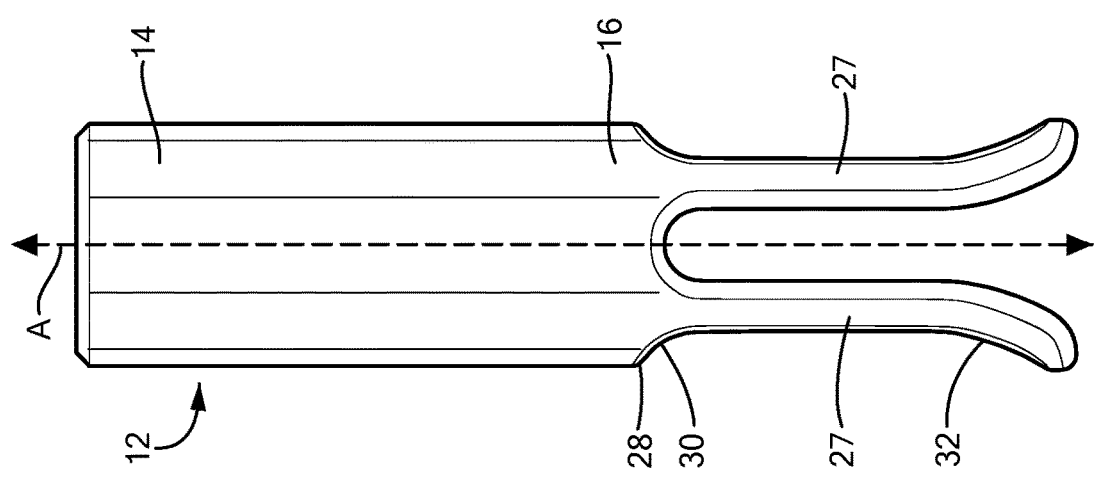
FIG. 2 is a front view of the body of the pressure sensitive device of FIG. 1.

With reference to FIG. 2, a front view of the body 12 is depicted in the constrained configuration. The distal portion 16 of the body 12 includes one or more expandable transition, for example a pair of arms or a first arm and a second arm, extending from a transition region 28 of the body 12. The transition region 28 includes a curved location in which the body 12 transitions from a tubular or cylindrical portion to the arms 27. The arms 27 are the portion of the distal end 16 configured to expand upon implantation into the blood vessel.

In one constrained configuration, the transition region 28 and the arms 27 define a first curved region 30 therebetween and the arms 27 define a second curved region 32 opposite the first curved region 30. The arms 27 in the second curved region 32 may be spaced a distance apart that is different from the distance between the arms 27 in the first curved region 30. Alternatively, the arms 27 in the second curved region 32 may be spaced the same distance apart as the arms 27 in the first curved region 30.

Figure 4:
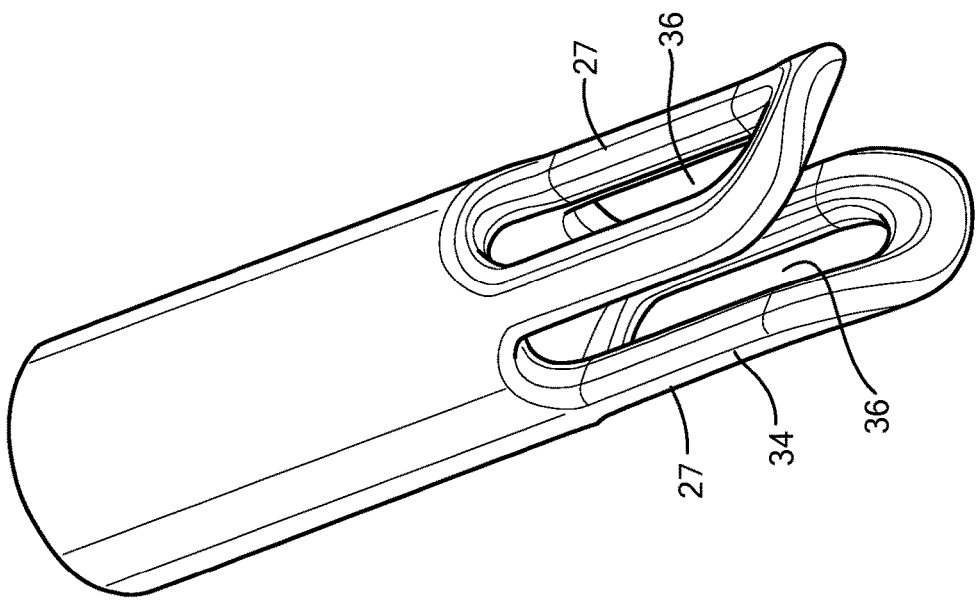
FIG. 4 is a perspective view of the body of the pressure sensitive device of FIG. 1.
Figure 3:
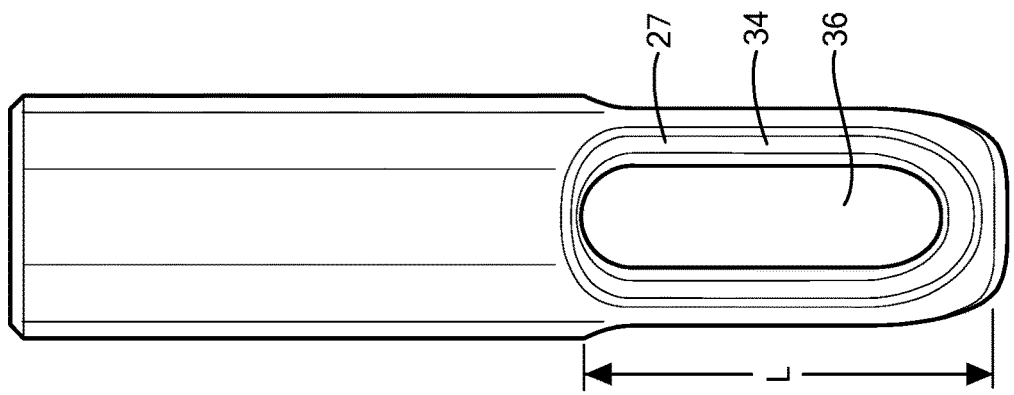
FIG. 3 is a side view of the body of the pressure sensitive device of FIG. 1.

With reference to FIGS. 3 and 4, the arms 27 each define a length "L" and a planar region 34 between the first curved region 30 and the second curved region 32 along the length. In addition, the planar region 34 at least partially defines an aperture 36 extending along the length. The relatively large surface area of the aperture 36 increases the surface area available for the fluid 22 when disposed within the fluid chamber 20 (FIG. 1). The size of the aperture 36 may be made larger or smaller depending upon the specific anatomy of the vasculature that the device 10 is going to be used with.

Figure 6:
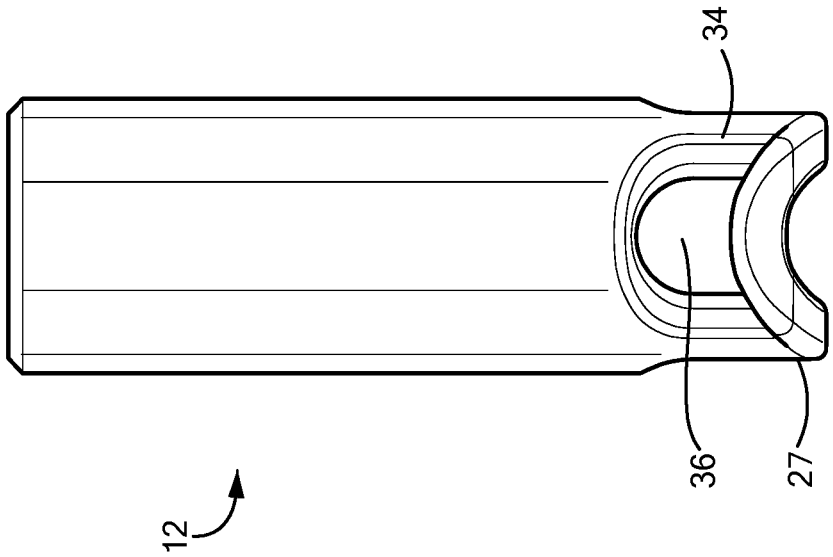
FIG. 6 is a side view of the body of the pressure sensitive device of FIG. 1.
Figure 5:
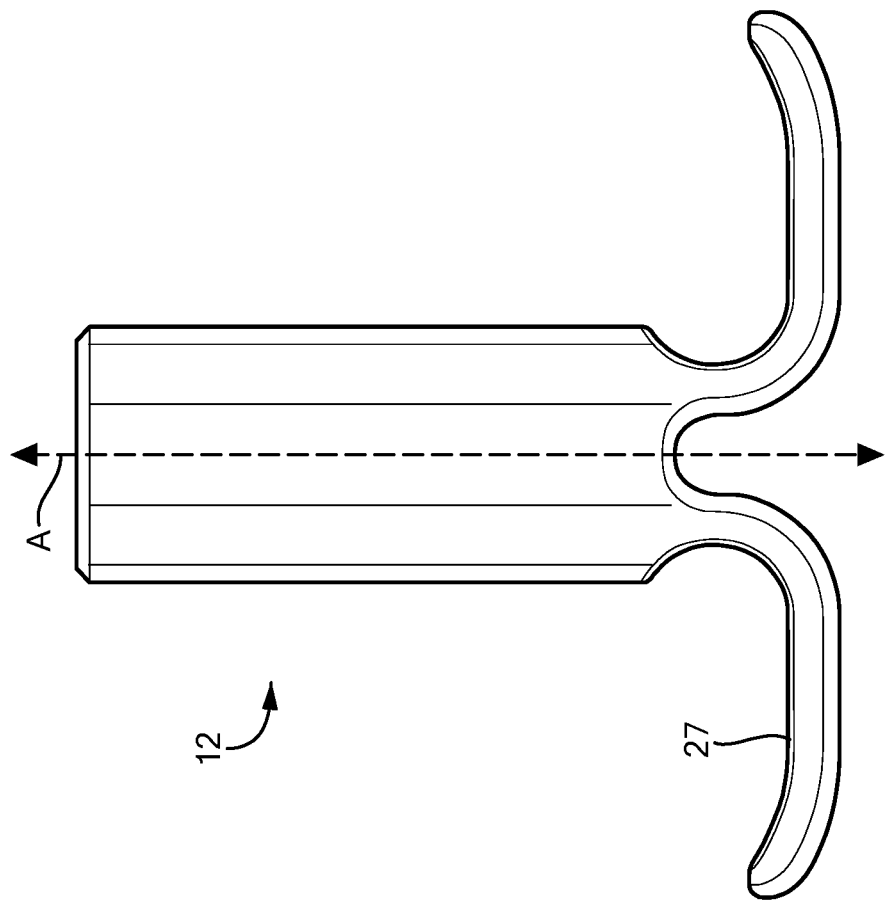
FIG. 5 is a front view of the body of the pressure sensitive device of FIG. 1.

Referring to FIGS. 5 and 6, the device 10 is depicted in the expanded configuration including the arms 27 being disposed transverse or perpendicular with respect to the axis A. As such, the expanded configuration is configured to provide the device 10 with a relatively larger surface area upon implantation than that which is provided in prior art devices configured as a pole, post, or the like.

In order to transition from the constrained configuration, in which the arms 27 are aligned and parallel with respect to the axis A, such as when within the delivery lumen (not shown) to the expanded configuration, the body 12 may be made of a self-expanding material or shape memory alloy, such as nitinol, i.e., nickel-titanium. A shape-memory alloy ("SMA") is generally defined as an alloy configured to remember or revert its original shape following a change in shape. For example, such alloy may undergo a phase transformation when under stress and return to its pre-transformed shape and phase when unstressed or heated. Shape memory alloys exhibit superelasticity, such as an elastic (reversible) response to an applied stress, that may be caused by a phase transformation between austenitic and martensitic phases of a crystal. Superelastic alloys belong to a relatively large family of shape-memory alloys. When mechanically loaded, a superelastic alloy deforms reversibly to relatively high strains, such as strains up to 10%, produced by the creation of a stress-induced phase. When the load is removed, the new phase becomes unstable and the material regains its original shape without the need for exposure to a change in temperature. Such material allows the body 12 to be transitioned from the constrained configuration to the expanded configuration without permanent deformation. In other words, the material may be super elastic to allow the body 12 to be constrained during delivery through the wall of the blood vessel and returned to the expanded configuration without being permanently deformed. The entire body 12 or a portion of the body including the proximal portion 14 and/or the distal portion 16 of the body may be made of a shape memory alloy. The device 10 may be inserted into the blood vessel in the constrained configuration and then transitioned from the constrained configuration to the expanded configuration once at least a portion of the device 10 is within the blood vessel. When the device 10 is to be removed from the blood vessel, the device 10 may be transitioned from the expanded configuration to the constrained configuration while inside the blood vessel to allow for easy removal of the device 10 from the blood vessel and to prevent any damage to the blood vessel.

Figure 7:
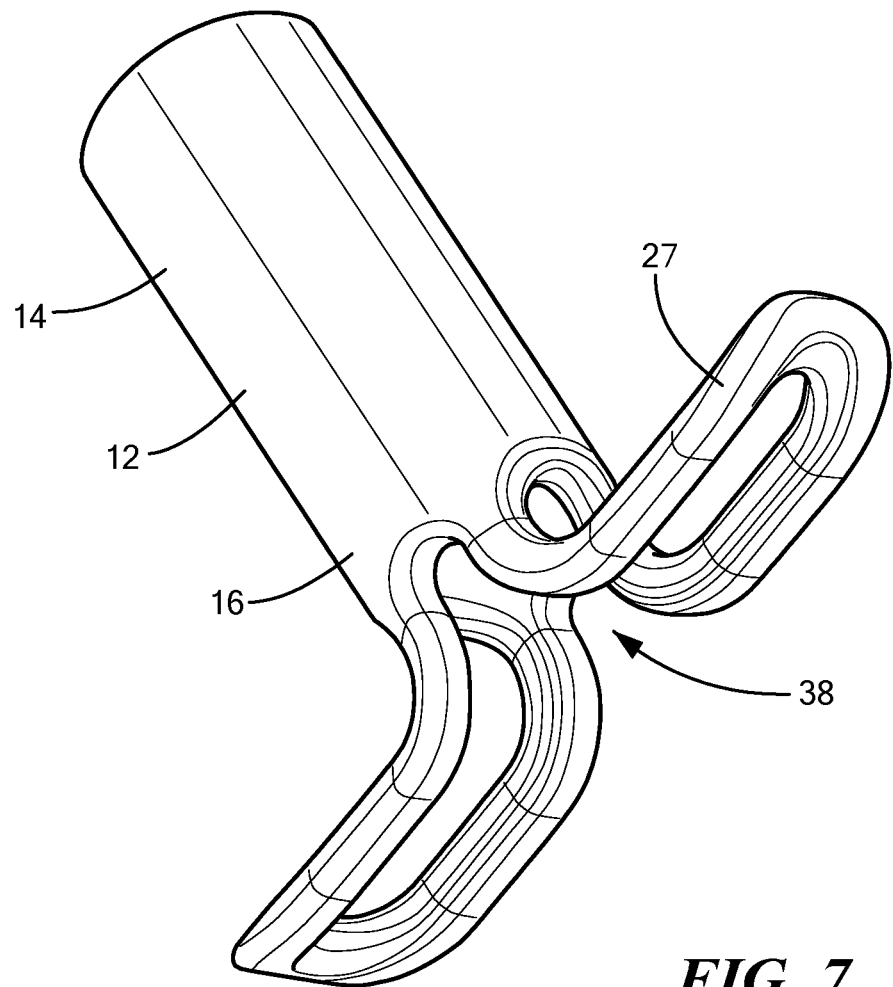
FIG. 7 is a perspective view of the body of the pressure sensitive device of FIG. 1.
Figure 8:
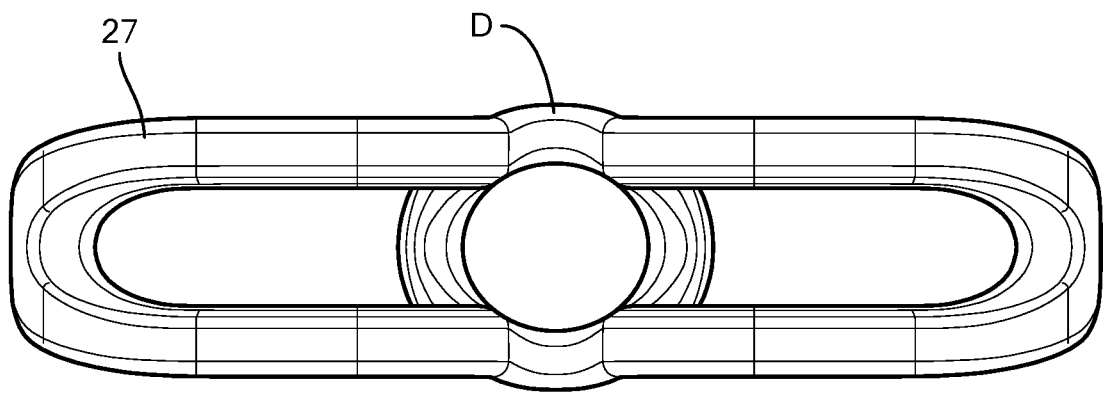
FIG. 8 is a bottom view of the body of the pressure sensitive device of FIG. 1.

With reference to FIGS. 7 and 8, the body 12 defines a fluid channel 38 extending from the proximal portion 14 to the distal portion 16 and the pressure measuring system 24 (FIG. 1) is in communication with the fluid 22 to measure the hydraulic pressure within the blood vessel. The dimensions of the fluid channel 38 may vary in accordance with the dimensions of the body 12. For example, in one configuration the body 12 defines an outer diameter "D" between 0.8 millimeters to 1.1 millimeters, however, other dimensions are within the scope of the present invention. The fluid channel 38 ends at a location in which the arms 27 extend away from each other when in the expanded configuration.

Figure 9:
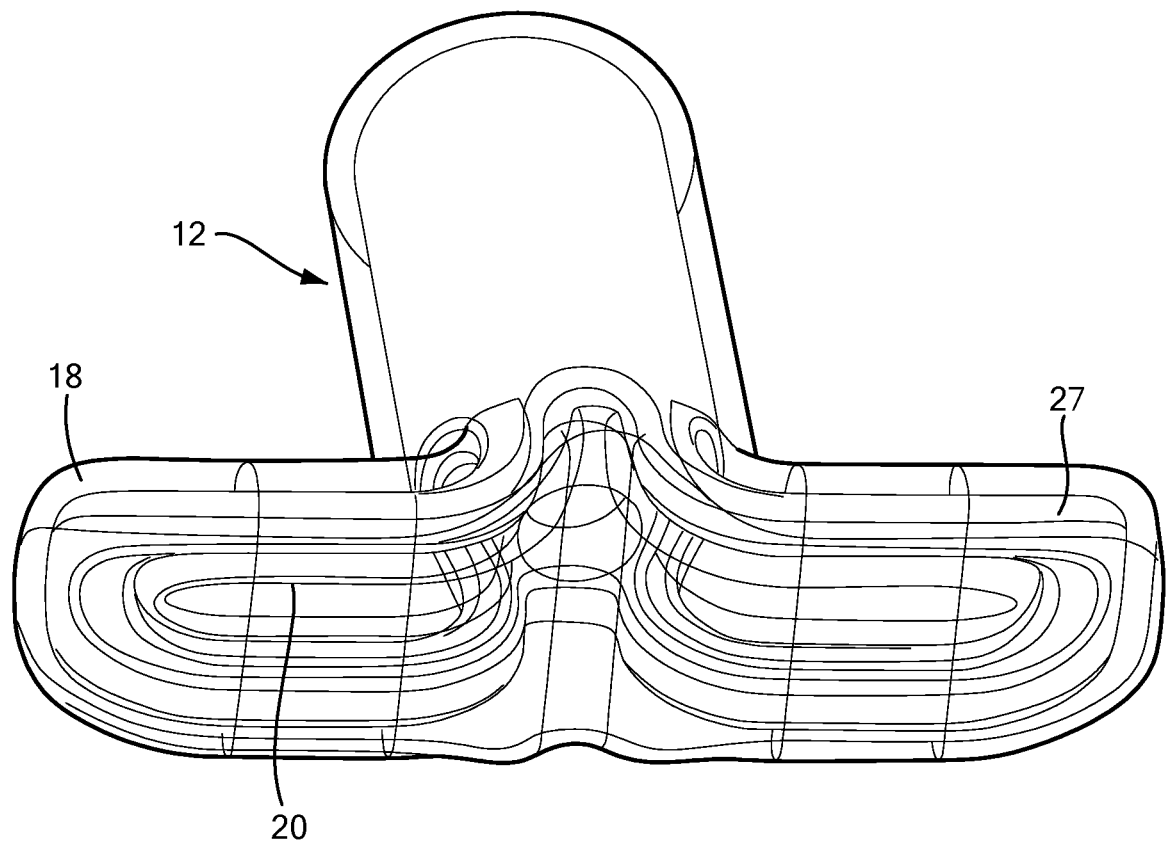
FIG. 9 is a front perspective view of the device of FIG. 1.

Referring to FIG. 9, a front perspective view of the body 12 is depicted including the diaphragm 18 surrounding the arms 27 to form the fluid chamber 20. As indicated above, the diaphragm 18 may be a compliant balloon, an elastomeric balloon, or a transduction balloon made of a material, for example a segmented polyurethane sold under the name Biospan®, molded over the body 12, and having a relatively large surface area in comparison to prior art devices, such as transvascular posts. The relatively large surface area is configured to maintain the sensitivity of the device 10 with respect to pressure measurements despite relatively small changes that may occur with respect to the mechanical properties of the device 10 and/or small changes that may occur in the volume of the fluid 22. The size and thickness of the diaphragm 18 may be configured to sense various pressure changes which may be large or small depending upon the particular anatomy of the patient.

Figure 10:
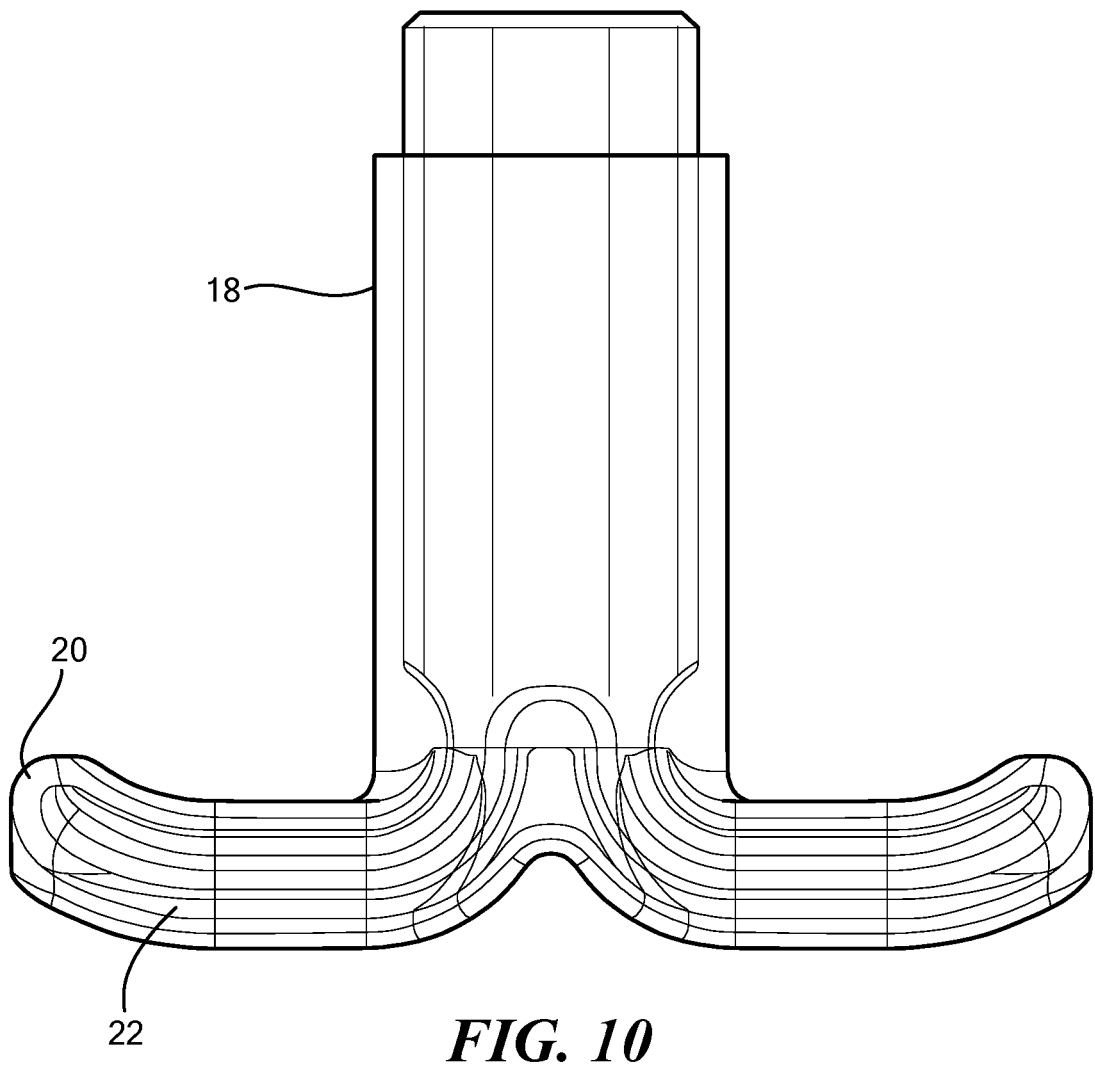
FIG. 10 is a front view of the device of FIG. 1 including a fluid disposed within the diaphragm.
Figure 11:
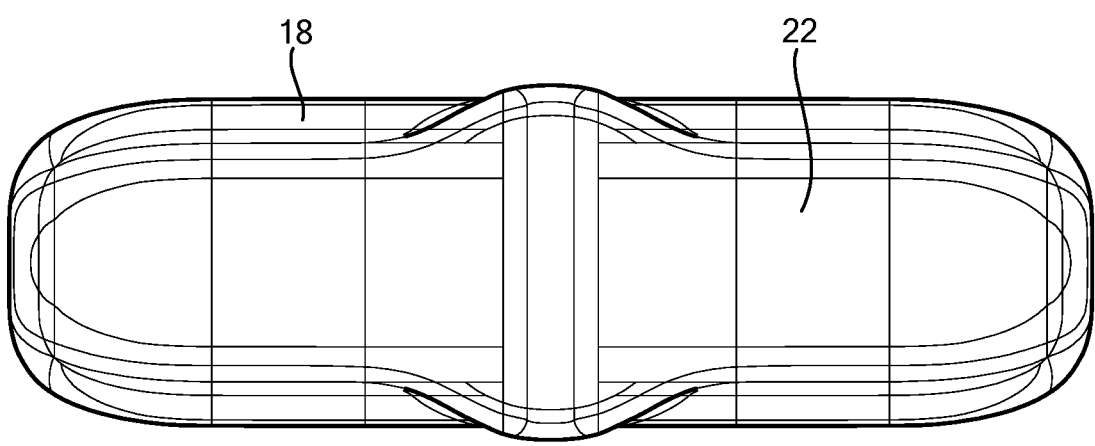
FIG. 11 is a bottom view of the device of FIG. 1 including the fluid disposed within the diaphragm.

In addition, as shown in FIGS. 10 and 11, the large surface area of the diaphragm 18 increases the capacity of the fluid chamber 20 to provide for added fill volume and thus account for fluid volume depletion over cycles of the fluid 22. The surface area of the diaphragm 18 may be customized to sense large and small pressure changes within a patient's vasculature.

Figure 12:
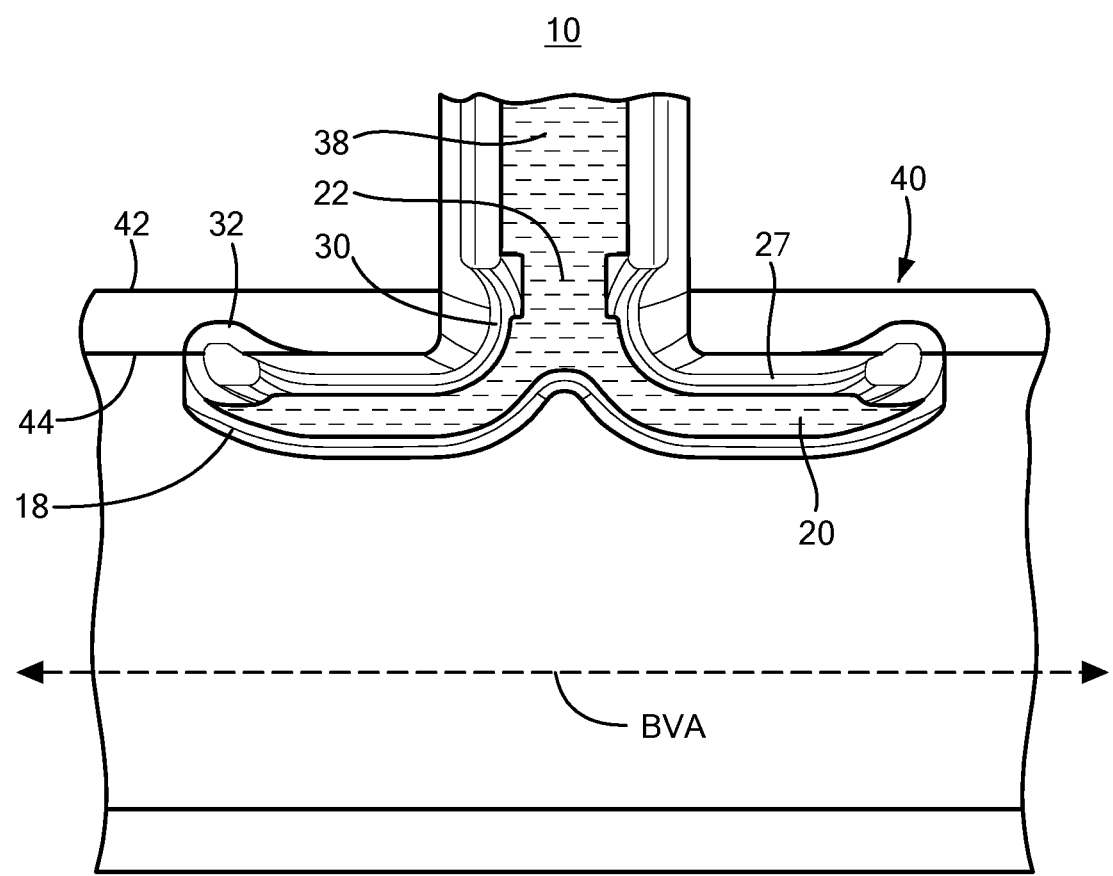
FIG. 12 is a front view of the device of FIG. 1 at least partially implanted within a blood vessel.
Figure 13:
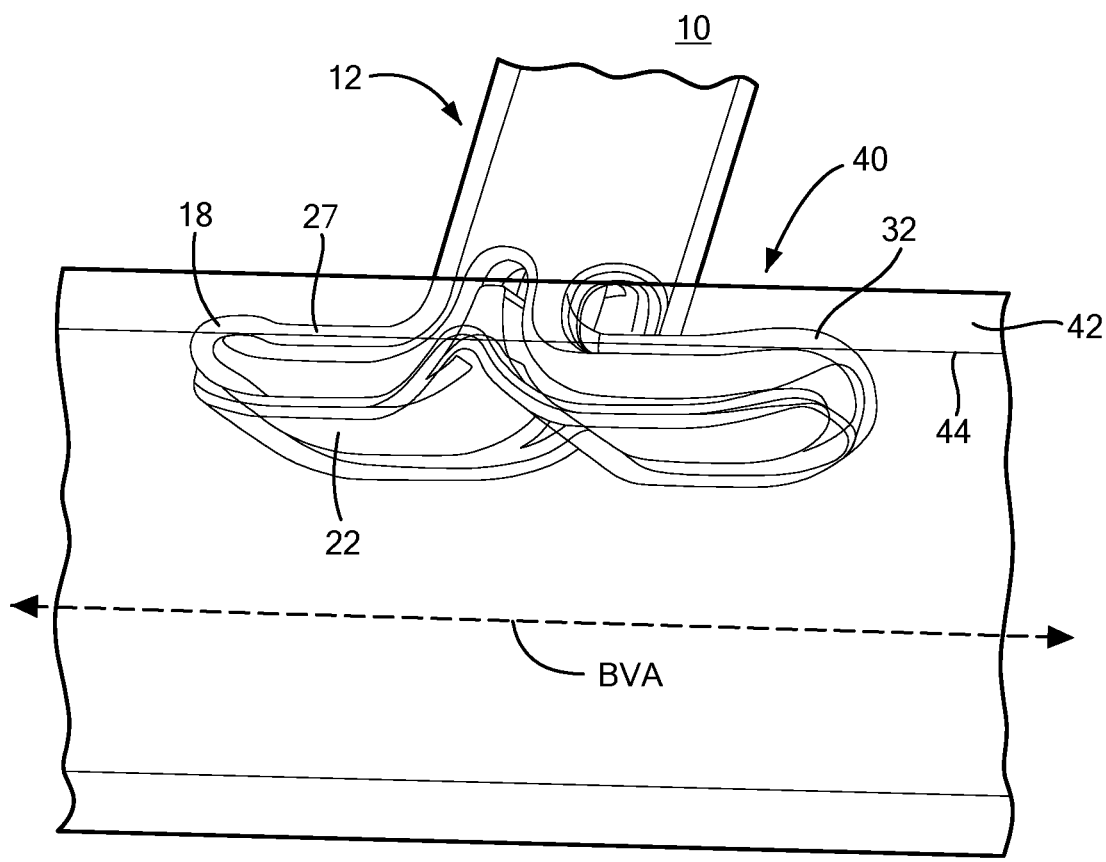
FIG. 13 is a perspective view of the device of FIG. 1 at least partially implanted within a blood vessel.

With reference to FIGS. 12 and 13, the device 10 is depicted including the arms 27 being implanted in an exemplary blood vessel 40 in the expanded configuration and surrounded by the diaphragm 18. The blood vessel 40 includes a wall 42 defining a blood vessel axis "BVA" extending parallel with respect to the wall 42. Upon implantation, the distal portion 16 of the body 12 extends through the blood vessel 40 with the proximal portion 14 being disposed in a transverse or perpendicular orientation with respect to the wall 42. When located within the blood vessel 40, the arms 27 are disposed parallel with respect to the blood vessel axis and configured to abut against an inner surface 44 of the wall 42 of the blood vessel 40. For example, FIG. 12 depicts the first curved region 30 and the second curved region 32 of the device 10 adjacent the wall 42 for minimal obstruction of blood flow. In an alternative configuration, the second curved region 32 of the device may be in contact with the wall 42 or secured to the wall 42 using a securing mechanism.

Figure 14:
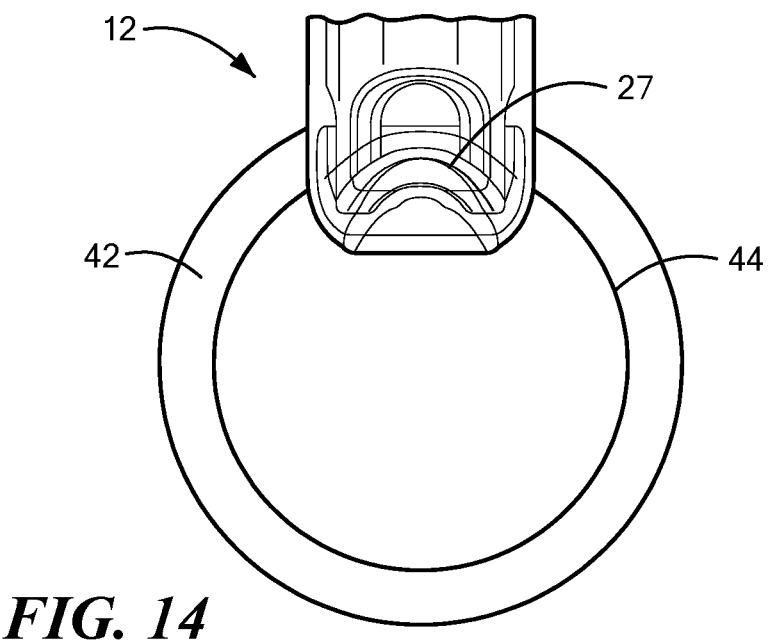
FIG. 14 is a side view of the device 10 at least partially implanted within a blood vessel.

In addition, the fluid 22 is disposed within the fluid channel 38 in fluid communication with the fluid chamber 20 for communicating the hydraulic pressure to the pressure measuring system 24 (FIG. 1), such as upon dilation and constriction of the blood vessel 40. In other words, as stated above, the fluid 22 is configured to communicate the hydraulic pressure exerted on the diaphragm 18 inside the blood vessel to the pressure measuring system 24 outside of the blood vessel. FIG. 14 depicts a side cross-sectional view of the blood vessel wall 42 including the arms 27 of the body 12 being adjacent thereto.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A pressure sensitive device comprising:
   a body including a proximal portion and a distal portion opposite the proximal portion, the distal portion being made of a shape memory alloy;
   a flexible diaphragm surrounding the distal portion of the body and defining a fluid chamber between the flexible diaphragm and the distal portion of the body; and
   a non-compressible fluid disposed within the flexible diaphragm and exhibiting a hydraulic pressure in communication with the flexible diaphragm.

2. The pressure sensitive device of claim 1, wherein the non-compressible fluid is fluidly coupled to a pressure measuring system remote from the body, the pressure measuring system being configured to measure the hydraulic pressure exerted by a force on the flexible diaphragm.

3. The pressure sensitive device of claim 1, wherein the proximal portion and the distal portion of the body define an axis extending therethrough, and the distal portion of the body includes a plurality of arms extending therefrom.

4. The pressure sensitive device of claim 3, wherein the body includes a constrained configuration and an expanded configuration, the constrained configuration including the plurality of arms being parallel to the axis and the expanded configuration including the plurality of arms being disposed transverse with respect to the axis.

5. The pressure sensitive device of claim 3, wherein the body includes a transition region having the plurality of arms extending therefrom.

6. The pressure sensitive device of claim 5, wherein the transition region and each arm from the plurality of arms defines a first curved region therebetween, and each arm from the plurality of arms defines a second curved region opposite the first curved region.

7. The pressure sensitive device of claim 6, wherein the plurality of arms each define a length and an aperture extending along the length.

8. The pressure sensitive device of claim 1, wherein the flexible diaphragm is an elastomeric balloon and the non-compressible fluid is a silicone.

9. A pressure sensing system comprising:
   a pressure sensitive device including:
      a tubular body having a transition region including a plurality of expandable arms extending therefrom, each arm from the plurality of expandable arms defining a length and each arm from the plurality of expandable arms defining a planar region extending at least partially along the length;

a diaphragm surrounding the plurality of expandable arms, the diaphragm defining a fluid chamber between the diaphragm and the tubular body;

a non-compressible fluid disposed within the fluid chamber and configured to exhibit a hydraulic pressure on the diaphragm; and a housing remote from and in communication with the pressure sensitive device, the housing including a pressure measuring system disposed therein, and the pressure measuring system including a Micro-Electro-Mechanic Systems ("MEMS") device configured to be in communication with the hydraulic pressure exhibited by the non-compressible fluid.

10. The pressure sensing system of claim 9, wherein the tubular body of the pressure sensitive device includes a proximal portion, a distal portion including the plurality of expandable arms opposite the proximal portion, and an axis extending therethrough.

11. The pressure sensing system of claim 10, wherein the plurality of expandable arms of the pressure sensitive device are made of a shape memory alloy and include an expanded configuration when disposed within a blood vessel, the expanded configuration including the plurality of expandable arms being disposed transverse with respect to the axis.

12. The pressure sensing system of claim 10, wherein the tubular body of the pressure sensitive device defines a fluid channel extending from the proximal portion to the distal portion.

13. The pressure sensing system of claim 9, wherein the transition region of the tubular body of the pressure sensitive device defines a first curved region and each arm from the plurality of expandable arms defines a second curved region opposite the first curved region.

14. The pressure sensing system of claim 13, wherein the planar region of each arm from the plurality of expandable arms of the pressure sensitive device is between the first curved region and the second curved region, and the first curved region partially defines an aperture extending along the planar region.

15. The pressure sensing system of claim 9, wherein the tubular body of the pressure sensitive device defines an outer diameter between 0.8 millimeters to 1.1 millimeters.

16. The pressure sensing system of claim 9, wherein the diaphragm of the pressure sensitive device is an elastomeric balloon and the non-compressible fluid is a silicone fluid.

17. The pressure sensing system of claim 9, further comprising a controller, a processor, and a power source, the pressure measuring system being in electrical communication with the controller, the processor, and the power source.

18. The pressure sensing system of claim 9, wherein the plurality of expandable arms of the pressure sensitive device include a pair of arms extending away from each other.

* * * * *